(12) United States Patent
Liu et al.

(10) Patent No.: US 11,701,072 B2
(45) Date of Patent: *Jul. 18, 2023

(54) MODULAR X-RAY SOURCE AND METHOD OF X-RAY SOURCE TUBE REPLACEMENT FOR MOTION COMPENSATED TOMOSYNTHESIS IMAGING SYSTEM

(71) Applicants: Jianqiang Liu, Campbell, CA (US); Manat Maolinbay, Gilroy, CA (US); Chwen-yuan Ku, San Jose, CA (US); Linbo Yang, Pleasanton, CA (US)

(72) Inventors: Jianqiang Liu, Campbell, CA (US); Manat Maolinbay, Gilroy, CA (US); Chwen-yuan Ku, San Jose, CA (US); Linbo Yang, Pleasanton, CA (US)

(73) Assignee: AlxSCAN, Inc., Sunnyvale, CA (US)

(*) Notice: Subject to any disclaimer, the term of this patent is extended or adjusted under 35 U.S.C. 154(b) by 22 days.

This patent is subject to a terminal disclaimer.

(21) Appl. No.: 17/533,631

(22) Filed: Nov. 23, 2021

(65) Prior Publication Data

US 2022/0369446 A1 Nov. 17, 2022

Related U.S. Application Data

(60) Provisional application No. 63/226,508, filed on Jul. 28, 2021, provisional application No. 63/225,194, (Continued)

(51) Int. Cl.
*A61B 6/00* (2006.01)
*H01J 35/18* (2006.01)
(Continued)

(52) U.S. Cl.
CPC .......... *A61B 6/4007* (2013.01); *A61B 6/4411* (2013.01); *A61B 6/025* (2013.01); *H01J 35/18* (2013.01); *H05G 1/06* (2013.01)

(58) Field of Classification Search
CPC ............................ A61B 6/4007; A61B 6/4411
See application file for complete search history.

(56) References Cited

U.S. PATENT DOCUMENTS 6,192,106 B1 * 2/2001 Miller .................... H01J 9/385
378/123
2004/0247080 A1 * 12/2004 Feda ........................ H05G 1/44
378/101
(Continued)

*Primary Examiner* — Chih-Cheng Kao
(74) *Attorney, Agent, or Firm* — Patent PC; Bao Tran

(57) ABSTRACT

A modular X-ray source and method for replacement of such an X-ray source are disclosed. The source is inside a consumable modular enclosure where the entire assembly is swapped out during maintenance. The enclosure covers an X-ray tube, high voltage circuit boards 6 and cooling insulating oil are arranged inside the module enclosure. The enclosure structure includes an X-ray window, connector engagement alignment guide and electrical connectors. The modular X-ray source is used in a multiple source tomosynthesis imaging system where multiple pulsed X-ray sources are utilized. The easy replacement of X-ray tube assembly inside the consumable modular enclosure results in lower maintenance cost and overall reliable X-ray imaging machine. The modular source has potential to increase the machine volume in the field and create new standards for replaceable modular X-ray source.

19 Claims, 6 Drawing Sheets

Related U.S. Application Data filed on Jul. 23, 2021, provisional application No. 63/224,521, filed on Jul. 22, 2021, provisional application No. 63/222,847, filed on Jul. 16, 2021, provisional application No. 63/220,924, filed on Jul. 12, 2021, provisional application No. 63/214,913, filed on Jun. 25, 2021, provisional application No. 63/209,498, filed on Jun. 11, 2021, provisional application No. 63/194,071, filed on May 27, 2021, provisional application No. 63/188,919, filed on May 14, 2021, provisional application No. 63/182,426, filed on Apr. 30, 2021, provisional application No. 63/175,952, filed on Apr. 16, 2021, provisional application No. 63/170,288, filed on Apr. 2, 2021.

(51) Int. Cl.
*H05G 1/06* (2006.01)
*A61B 6/02* (2006.01)

(56) References Cited

U.S. PATENT DOCUMENTS

| | | | |
|---|---|---|---|
| 2005/0175150 A1* | 8/2005 | Smith | H05G 1/02 378/119 |
| 2005/0208820 A1* | 9/2005 | Sanuki | H01R 13/623 439/372 |
| 2006/0098778 A1* | 5/2006 | Oettinger | H05G 1/10 378/101 |
| 2012/0051500 A1* | 3/2012 | Johansson | A61B 6/0414 378/22 |
| 2014/0050305 A1* | 2/2014 | Zhao | H01J 35/13 378/141 |
| 2014/0126696 A1* | 5/2014 | Xu | G01T 1/295 378/62 |
| 2015/0098552 A1* | 4/2015 | Draper | H05G 1/06 378/142 |
| 2015/0124936 A1* | 5/2015 | Anno | H01J 35/106 378/130 |
| 2018/0190465 A1* | 7/2018 | Huang | H01J 35/08 |
| 2020/0100747 A1* | 4/2020 | Matsuura | A61B 6/107 |

* cited by examiner

MODULAR X-RAY SOURCE AND METHOD OF X-RAY SOURCE TUBE REPLACEMENT FOR MOTION COMPENSATED TOMOSYNTHESIS IMAGING SYSTEM

The present invention claims priority to Provisional Application Ser. Nos. 63/182,426 filed on Apr. 30, 2021; 63/226,508 filed Jul. 28, 2021; 63/170,288 filed Apr. 2, 2021, 63/175,952 filed Apr. 16, 2021, 63/194,071 filed May 27, 2021; 63/188,919 filed May 14, 2021; 63/225,194 filed Jul. 23, 2021; 63/209,498 filed Jun. 11, 2021; 63/214,913 filed Jun. 25, 2021; 63/220,924 filed Jul. 12, 2021; 63/222,847 filed Jul. 16, 2021; 63/224,521 filed Jul. 22, 2021; and U.S. application Ser. No. 17/149,133 filed Jan. 24, 2021, which in turn claims priority to Provisional Ser. 62/967,325 filed Jan. 29, 2020, the content of which is incorporated by reference.

FIELD OF THE INVENTION

This application generally relates to X-ray generation equipment, and more particularly to a small, lightweight, and power-efficient X-ray source module.

BACKGROUND

X-ray sources have wide applications in medical, industrial, security, and other scientific and technical fields. In most cases, there is one X-ray source in one X-ray imaging machine. However, in some cases, multiple X-ray sources are needed in a single machine with specific fast imaging applications. Multi-Source X-ray Tomosynthesis Imaging System is becoming popular, as it can create 3D images with high speed and a low dose rate. Because it uses multiple pulsed X-ray sources in motion, it is necessary to make X-ray source modular to perform easy replacement. X-ray source tube assembly is completely prefabricated offsite. The on-site installation involves only the basic connecting of utilities.

When more X-ray sources are used in a single machine, more reliability issues will come up. If one X-ray source fails among multiple other X-ray sources, then the machine overall will malfunction.

There are two ways to address this kind of problem. One is to increase the reliability of an X-ray source itself by enhancing the reliability of every X-ray source component so that a machine can become more reliable overall. The other way is to create a new process, so that replacement of machine components is easy and low cost so that no special personnel training is needed.

However, some critical components are consumables and are known to always have a finite lifetime no matter how technology advances. For example, nobody expects a standard light bulb will last forever. Nowadays, in most cases, every adult with an ordinary skill is able to replace a standard light bulb.

Similarly, an X-ray tube of an X-ray source is the most consumed component inside an X-ray machine. It has a finite lifetime. However, in prior art, it is technically difficult to replace an X-ray tube in a portable and mono-block types of X-ray sources. Special tools are usually needed, and even a cleanroom is needed in some cases because of possible insulation oil contaminations. X-ray tubes are one type of high voltage devices. It is an industry practice to discharge static electricity on operators before working with them. However, X-ray tubes are not dischargeable. There are three general reasons. First, no safety mechanism inside the X-ray tube exists for discharging extra charge. Second, there is no way to easily do that outside of the X-ray tube either. A significant amount of insulation oil (10~20 cm) usually covers the X-ray tube surface. Some stray static electricity cannot pass through that oil layer. Furthermore, some metal parts may exist on the enclosure structure. If they are accidentally touched during the detaching process, they can form additional capacitance and result in an electrostatic discharge to the operator. Even if any extra charge is discharged, it will be like a needle prick or less, which can be ignored without human recognition. Third, even though no extra charge is generated inside the X-ray tube, operating personnel have to wear conductive rubber gloves. If the gloves are made of synthetic materials, then their conductivity will be very low. The capacitance between the X-ray tube enclosure structure and the X-ray tube window is very high because of the small gap. So, if gloves are accidentally touched during the detaching process, they will become the conductive path to the high voltage part. Without external grounding equipment, electrostatic charge can cause undesired events. There are two different kinds of X-ray sources used in the X-ray imaging system in prior art. One is portable type source, the other is a mono-block type source.

Further, special personnel training is needed to replace the tubes in prior art. Even if a technical person understands the detailed knowledge of an X-ray tube in general, special training is still needed for a specific brand of X-ray source. Technical difficulties and special training requirements can add up costs vary significantly and quickly.

SUMMARY

Modular X-ray source and method for replacement of such an X-ray source, in which a consumable X-ray tube, a high-voltage circuit and cooling insulating oil are arranged inside a pre-designed module enclosure structure. There is an X-ray tube window, alignment guide, and electrical connector on the module enclosure structure. The enclosure usually is made of low-cost extrusion aluminum and welded at both ends. The modular X-ray source is particularly useful for motion compensated multiple pulsed source tomosynthesis imaging system where X-ray sources are utilized, easy replacement of X-ray tube, lower maintenance cost, reliable X-ray imaging system up-and-running time are required.

The modular X-ray source has a number of advantages. One advantage is that, due to the modular enclosure with the X-ray tube assembly, it is very easy to replace the whole enclosure of X-ray tube assembly at a very low cost without special personnel training needed, because technical difficulties and special training requirements can add up costs vary significantly and quickly. Another advantage is that it only takes very quick time to replace during the repair process with very few mechanical and electrical steps to follow. The system enables a new X-ray standard so technical personnel do not have to be familiar with different kinds of X-ray sources. The current invention has many advantages. The modular system has X-ray tube, high voltage circuits, insulation, and cooling oil etc., are all built inside an enclosure. There are only electrical connectors and alignment guides to deal with for a user, it can makes the X-ray source servicing as easy as replacing a standard light bulb. The design of modular X-ray source is suitable for high-volume production. Motion compensated multiple pulsed X-ray source tomosynthesis imaging system is intended for low cost fast 3D imaging worldwide, so the X-ray source volume can be very large. Cost of X-ray source can go even much lower when the volume is up. A lower cost can in turn generate even higher volume. Then cycle of lower price to higher volume is a virtuous cycle to generate good results.

BRIEF DESCRIPTION

DETAILED DESCRIPTION

Figure 1:
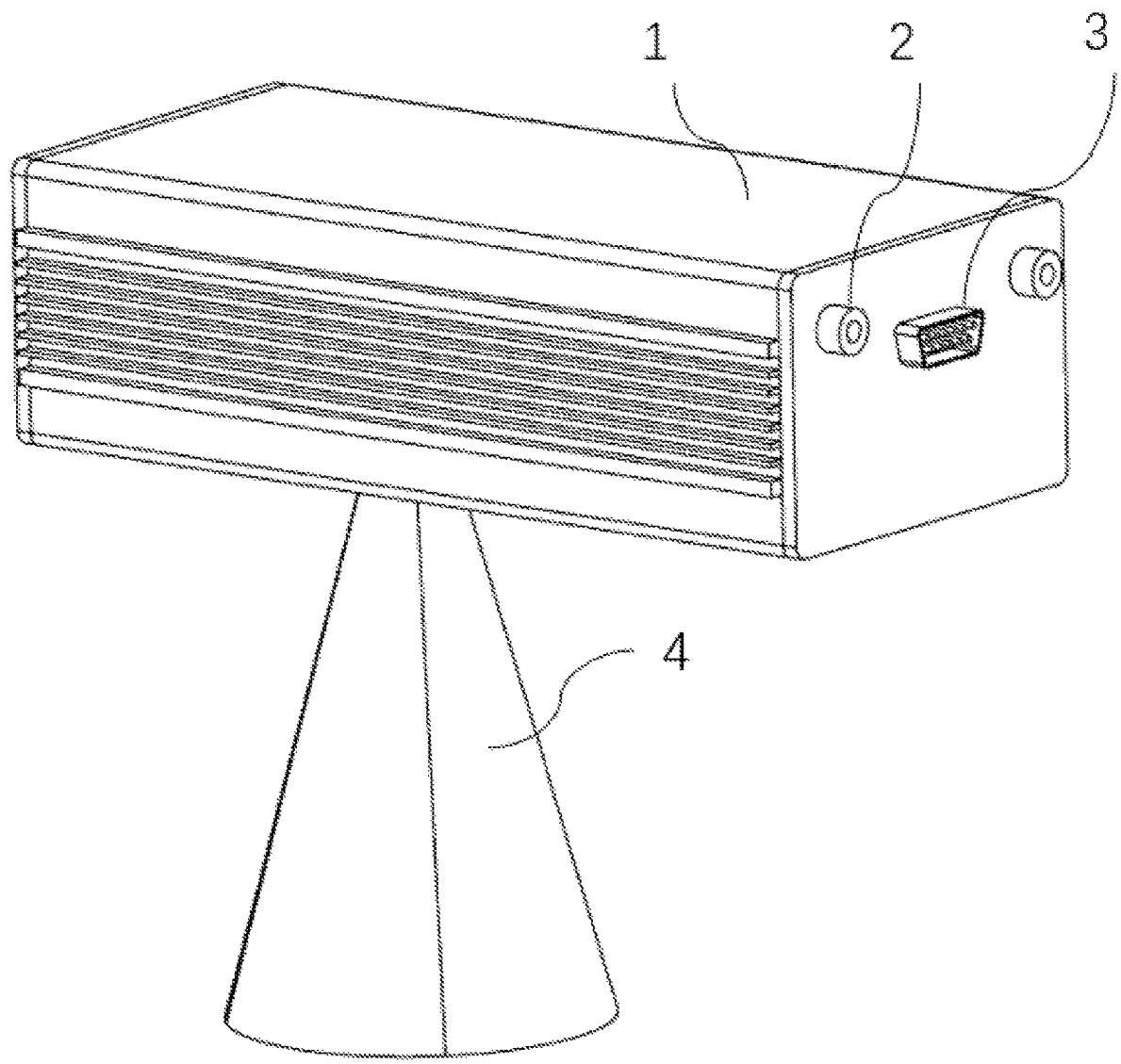
FIG. 1 illustrates a replaceable X-ray tube assembly of modular X-ray source.

The present invention will be described in detail by way of example with reference to the attached drawings. Throughout this description, the preferred embodiment and examples shown should be considered as exemplars, rather than as limitations on the present invention. As used herein, the "present invention" refers to any one of the embodiments of the invention described herein, and any equivalents. Furthermore, reference to various feature(s) of the "present invention" throughout this document does not mean that all claimed embodiments or methods must include the referenced feature(s).

This invention now will be described more fully hereinafter with reference to the accompanying drawings, in which exemplary embodiments are shown. Various embodiments are now described with reference to the drawings, wherein such as reference numerals are used to refer to such as elements throughout. In the following description, for purposes of explanation, numerous specific details are set forth in order to provide a thorough understanding of one or more embodiments. It may be evident, however, that such embodiment(s) may be practiced without these specific details. In other instances, well-known structures and devices are shown in block diagram form in order to facilitate describing one or more embodiments.

Thus, for example, it will be appreciated by those of ordinary skill in the art that the diagrams, schematics, illustrations, and such as represent conceptual views or processes illustrating systems and methods embodying this invention. The functions of the various elements shown in the figures may be provided through the use of dedicated hardware as well as hardware capable of executing associated software. Similarly, any switches shown in the figures are conceptual only. Their function may be carried out through the operation of program logic, through dedicated logic, through the interaction of program control and dedicated logic, or even manually, the particular technique being selectable by the entity implementing this invention. Those of ordinary skill in the art further understand that the exemplary hardware, software, processes, methods, and/or operating systems described herein are for illustrative purposes and, thus, are not intended to be limited to any particular named manufacturer.

Figure 3:
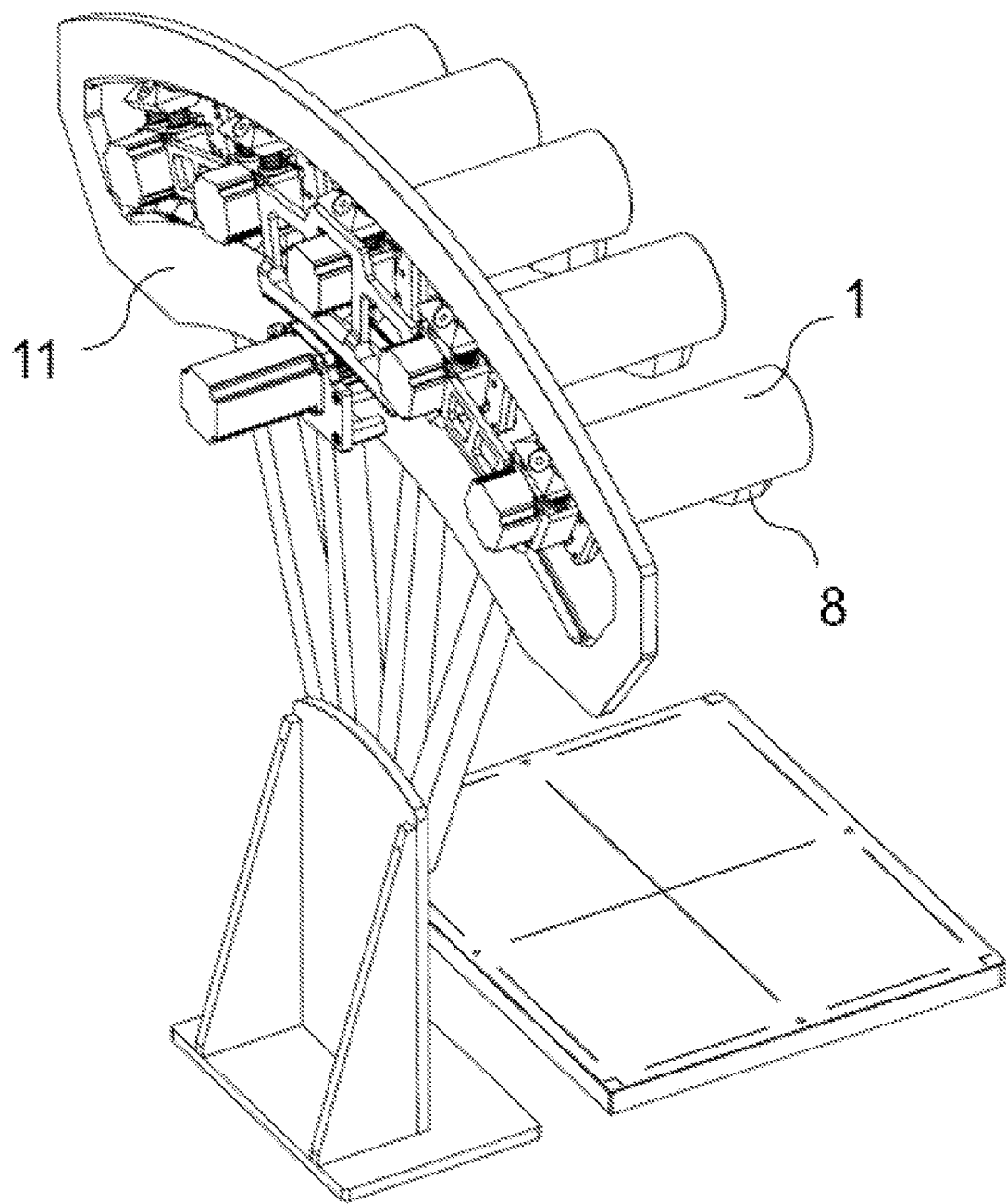
FIG. 3 illustrates a motion compensated multiple pulsed X-ray source tomosynthesis imaging system where multiple pulsed X-Ray sources are used in a single machine.

FIG. 3 shows a novel type of X-ray imaging system to perform high-efficient and ultrafast 3D radiography. It is called a motion compensated multiple pulsed X-ray source tomosynthesis imaging system 11. There are multiple pulsed X-ray sources mounted on a structure in motion to form an array of sources. Each pulsed X-ray source comprises X-ray tube assembly 1 body and external electronics. The multiple X-ray sources move simultaneously relative to an object on a predefined arc track at a constant speed as a group. Each individual X-ray source can also move rapidly around its static position at a small distance. When an X-ray source has a speed equal to group speed but with opposite moving direction, the X-ray source and X-ray flat panel detector are activated through an external exposure control unit so that source stays momentarily stand still. It results in much-reduced source travel distance for each X-ray source. 3D scan can cover a much wider sweep angle in a much shorter time, and image analysis can also be done in real-time. This type of X-ray machine utilizes much more X-ray sources than other types of X-ray image machines in order to achieve a much higher scan speed. Because multiple sources are used, it is necessary to ensure that every X-ray tube is functioning so that the whole machine is running.

Multiple X-ray sources are mounted on a rotating gantry. Each X-ray source emits a pulsed X-ray beam 4 toward an object. The frame structure includes multiple source frame segments. Each has multiple pulsed X-ray tube sources. A plurality of source segment holders is used to hold the individual source segments at a predetermined location in a certain shape of arc. An overall group of sources is held by an overall structure designed to move along the direction of an arc. An arc rail with a predefined curvature is provided as a guide and track to support the motion of the overall structure. A source activating controller is connected to the X-ray flat panel detector and each X-ray tube of the sources to trigger each X-ray tube individually.

The X-ray flat panel detector is configured to generate image data in response to X-ray electromagnetic radiation transmitted from the X-ray source. Although the example embodiment of the invention disclosed herein is described with respect to an X-ray flat panel detector, it should be understood that the detector may also be of any other type of detector known in the art without departing from the scope of the present invention.

Figure 4:
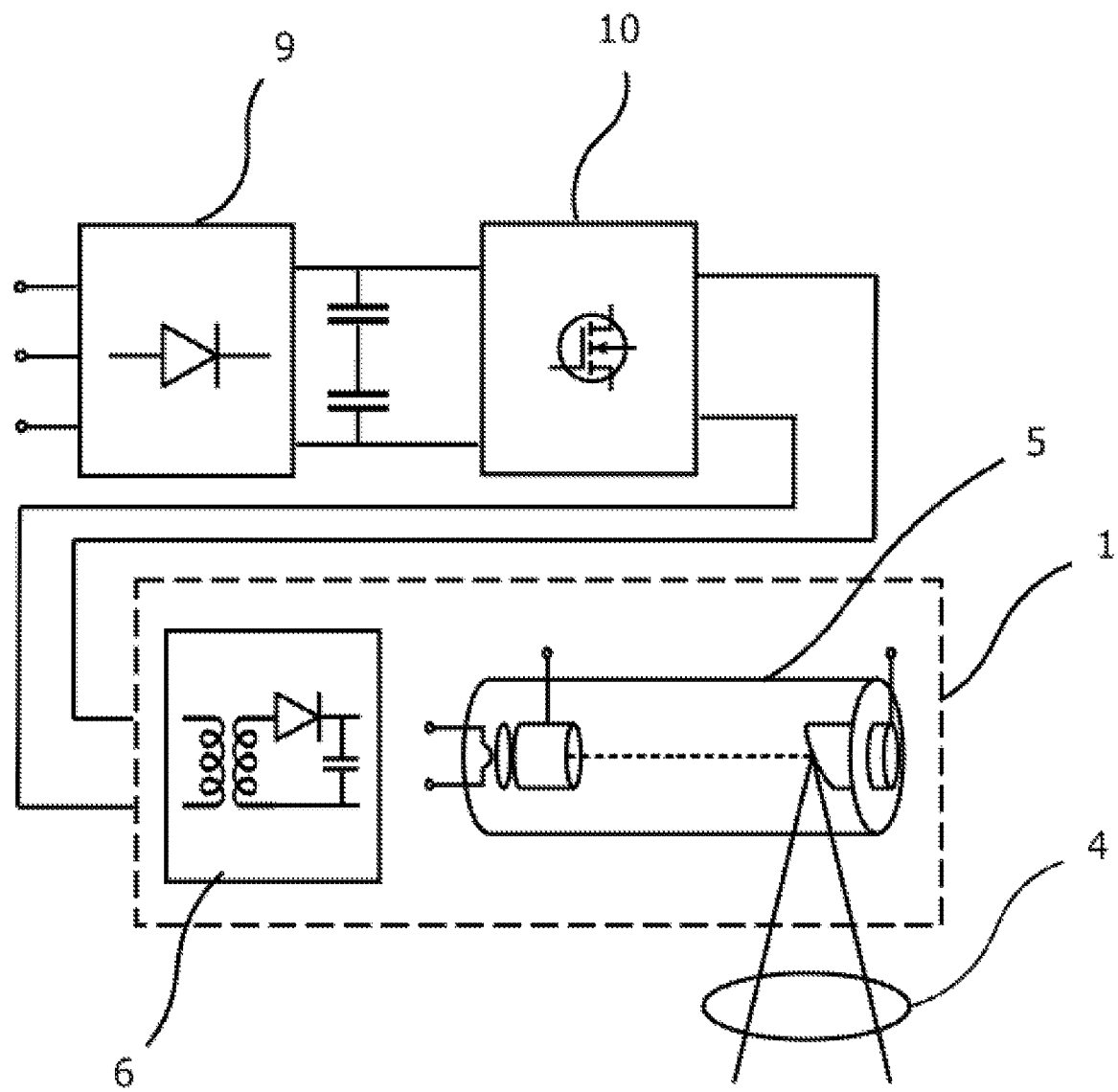
FIG. 4 illustrates an explanatory electrical diagram of a modular X-ray source.

FIG. 4 illustrates an exemplary X-ray source diagram with various elements. Starting from input of standard 110V AC or 220 AC power supply, the user-replaceable modular unit includes an X-ray source with a main rectifier 9, inverter 10, high voltage circuit board 6 and X-ray tube 5 etc. X-ray tube 5 and high voltage circuit board 6 can be assembled by a single manufactured unit that has several connected components inside a sealed enclosure to form an X-ray tube assembly 1 body so that it is consumable to replace on-site if necessary. The enclosure can have some mounting holes on its exterior for easy installation. This assembly of electrical connectors 3 with an alignment guide 2 is located on the enclosure's exterior for easy accessibility during the replacement process. A window on the enclosure is an X-ray window 8 with a protective layer on the front surface. For motion compensated X-ray tomosynthesis imaging system, multiple similar modules are built into one whole system. It is intended for this kind of module design to address the current deficiencies of the prior art of modular X-ray source systems. Currently, there are several modules available on the market, but they are all relatively expensive compared to this invention. Most of them are "modular" because they are relatively portable.

There are several key advantages of this invention. The first advantage is that technically it is very easy to replace X-ray tube assembly 1 in the modules of this invention. The second advantage is that there are no special tools needed. Just using some alignment guide is sufficient. The third advantage is that there are no special personnel training needed. The fourth advantage is that because everything is made inside an enclosure, all insulation contamination problems are taken care of.

X-ray tube 5 is mounted to the internal front side of the X-ray tube assembly 1. There is high voltage circuit board 6 and insulating oil inside the module. X-ray tube, high voltage circuit board 6 and insulating oil are placed inside an enclosure. The enclosure can be made of aluminum alloy or similar material. It is either stamped out or molded into an extrusion shape or similar shape. The enclosure has X-ray window 8, alignment guide 2, and electrical connectors 3. X-ray window 8 allows the passage of the radiation coming from X-ray tube 5 out to a patient or a scan object. Electrical connectors 3 are for connecting high voltage circuit board 6 and filament of the X-ray tube 5. An alignment guide 2 is used to make sure that electrical connectors 3 is fully seated and X-ray tube assembly 1 is aligned to the collimator, X-ray detector etc.

High voltage circuit board 6 drives X-ray tube 5 to generate X-ray beam 4 which is emitted from X-ray tube window 8. Electrical connectors 3 provide low resistance paths for the flow of electrical current from external main rectifier 9 and inverter 10 to high voltage circuitry 6 and X-ray tube 5. There is front cover and rear cover as part of the rear enclosure. main rectifier 9 and inverter 10 are electronic control boards on which the components such as semiconductor chips and diodes, coils and capacitors etc., can be assembled.

DC high voltage is used in the motion compensated multi-source X-ray tomosynthesis imaging system. These high voltages can be achieved with an voltage multiplier circuit with various transformer ratios of multiples plus rectifier, with air or vacuum gaps depending on the application requirements. The operating current varies with switching times ranging from tens of microseconds to tens of milliseconds. When an X-ray tube lifetime is short enough, most systems will become problematic. Other than this, other machine components also need to be replaced due to so many failure reasons and their consequences. If it were not a problem before X-ray tube 5 replacement, X-ray source life would be only about ⅓ of its original expected service life after 10 years. Many other components inside an X-ray machine, such as mechanical parts, wiring, and insulating oil, also contribute to failure problems. However, their contribution is less than that of an X-ray tube 5.

AC voltage is from standard 110V AC or 220 AC power supply. The AC high voltage is supplied to the cathode side of X-ray tube via an isolating device such as transformer. It is particular useful for a motion compensated tomosynthesis imaging system where multiple pulsed X-ray sources are utilized, easy replacement of X-ray tube assembly 1, lower maintenance cost, reliable X-ray imaging system up-and-running time are required. Regarding low-cost modular X-ray source module enclosure structure, X-ray tube window 8 is provided at one end of module enclosure. X-ray tube window 8 provides an X-ray path from the inside module enclosure to the outside world. One or more alignment guides 2 are provided at the same end of the electrical connector 3.

Cathode controller communicates with the control unit to control a hold voltage to be applied to a filament as the electron emitter. As it is heated up the increased energy enables electrons to be released from the filament through thermionic emission. The electron emitter is operatively connected to the cathode controller and the power supply so that the electron emitter can emit electrons at a controllable level.

High voltage generator produces high voltage pulses in output terminal through trigger pulse and width control signal. These high voltage pulses can be applied to X-ray tube and produce x-rays at the end of X-ray tube 5 as output X-ray beam 4 for use in medical imaging and other applications. The X-ray tube 5 is mounted to the module shell enclosure and located within the enclosure. This portable and small-size X-ray tube assembly 1 have many advantages, such as very easy maintenance and reliability, replaceable just like light bulb.

Electrical control can be any kind of electrical device or any circuit so long as it is able to control the high voltage to go to X-ray tube 5. However, in one embodiment, electrical control is low voltage part and mostly located outside of X-ray tube assembly 1. Low voltage part of control circuit is usually stable and lasts much longer. The prefabricated X-ray tube assembly 1 modules can be individually shipped with proper packing to the X-ray imaging system company's facility to build new X-ray source or repair old ones. Usually, X-ray tube 5 is mounted it the machine body already. Next, an insulation stand for safety purposes is set up near an assembly with old X-ray tube. On the insulation stand, an old X-ray tube module enclosure can be removed X-ray machine. After that, user can pull out an X-ray tube assembly 1 from X-ray machine. To put back a new X-ray tube assembly 1, user just aligns electrical connector 3 on module enclosure using alignment guide 2. After new X-ray tube assembly 1 is fully seated, power switch then can be turned on.

Most commonly, a standard smaller X-ray tube 5 is used for a multi-source tomosynthesis imaging system. In other words, a standard smaller X-ray tube 5 is used for medical and security applications to generate better resolution with the lowest dose rate. Sometimes, a large diameter X-ray tube 5 has been traditionally preferred in the clinical field. However, for this invention, there is no limitation on the shape of an X-ray tube 5. Usually, a small diameter X-ray tube 5 is used in medical, and security applications for a small area target, while a larger diameter X-ray tube 5 is used in industrial applications. An X-ray tube 5 operates in an oil-insulated chamber in most cases.

An electrical connector 3 with multiple contacts is arranged on one end of the X-ray tube assembly 1 enclosures. The connector allows electrical connection to an electronic device. A window is arranged towards the other end of the X-ray tube assembly 1 enclosure. An alignment guide 2 is arranged on one side of the X-ray tube enclosure. The alignment guide 2 is used to align the X-ray tube assembly 1 enclosure to a holding device in X-ray machine. The holding device can be an apparatus for holding and replacing the X-ray tube assembly 1 and/or an X-ray source body. The X-ray tube assembly 1 enclosure also has an X-ray tube 5 chamber inside enclosure. In one embodiment, the X-ray tube 5 chamber contains one or more than one consumable X-ray tubes 5. In another embodiment, the X-ray tube 5 chamber contains one or more than one non-consumable X-ray tubes 5. In some embodiments, the X-ray tube 5 chamber contains a combination of consumable and non-consumable X-ray tubes 5.

High voltage is applied to an insulated electrode and a hot cathode filament. In some systems, a control grid controls the beam of electrons emitted from the filament. When the wire is sufficiently heated, a discharge takes place between the wire and a reflector, forming a cloud of electrically charged gas. As the cloud of charged gas expands into an evacuated space, a stream of electrons is formed that can strike the second anode, depending on the polarity of the high voltage supply. When struck by the stream of electrons, the anode emits X-rays on the side of the source module.

Electrical control controls the amount of electric power supply for X-ray tube 5 and high voltage circuits based on the control signal received from the control computer. Control computer can calculate X-ray beam 4 isocenter position in an object to be imaged according to imaging algorithm, and then control electrical control to achieve desired X-ray output with controlled high voltage level and current flow through X-ray tube 5 and high voltage circuit. Voltage level and current flow in high voltage circuit can be adjusted and controlled by adjusting and controlling energy density and energy fluence.

X-ray tube 5 is usually cylindrical. In order to optimize efficiency, it has been cut to the desired length. X-ray tube shielding envelope is a protective layer surrounding X-ray tube and may be made of a suitable material such as a heavy metal or ceramic. Although the exact composition of the envelope is not important for the operation of the tube, a thick envelope can help absorb more radiation from the electrons as they lose energy passing through the envelope.

In some embodiments microcontroller controls an X-ray beam 4 generator, which may include an X-ray tube 5. The microcontroller is configured to control the timing and firing of the X-ray beam generator to produce an X-ray beam 4 for exposing an object, such as the patient. Control parameters, for example, voltage, current, angle, X-ray tube potential, frame rate, window shape, window thickness, source-to-surface distance, duration of the X-ray beam 4, energy, contrast level, etc., may be selected, modified, or controlled by input received from operator console via input/output circuitry. The microcontroller also may be configured to communicate with other imaging system components via communication circuitry.

Enclosure of most designs in prior arts use thick wall stainless steel to make a very sturdy high-cost enclosure. Two positioning screw holes are placed in the middle of the bottom part. The positioning screw holes are used to accurately position X-ray tube 5 when it is installed inside the enclosure. There are several alignment pins. Three alignment pins are in three different parts of the enclosure. One pin is in one side plate, another pin is in the opposite side plate, and the third alignment pin is in the bottom plate. This ensures proper X-ray window 8 alignment when an X-ray tube 5 is assembled into the enclosure. A crossbar can be used to support X-ray tube 5. The crossbar has special features for improved gripping.

FIG. 1 indicates that outside the enclosure of an X-ray tube assembly 1, there are only multi-pin electrical connectors and connector guides for easy connector pin engagement alignment. Using this kind of X-ray tube assembly 1, all users need to do is to pull out older ones and put them back in new ones, just like replacing an advanced light bulb set. For X-ray tube 5 with different power, the size of X-ray tube assembly 1 can be different. In general, a higher power X-ray tube 5 would have a larger size than that of less powerful X-ray tube 5. Therefore, the size of the enclosure would also be larger for higher power X-ray tube 5.

X-ray tube assembly 1 enclosure contains X-ray tube 5. Cooling insulation insulates an interior of the X-ray tube assembly 1 enclosure from an exterior environment. Insulation and cooling fluid are usually oil. X-ray tube assembly 1 enclosure includes a top plate, bottom plate, front plate, backplate, upper module frame, lower module frame, left end cap, right end cap, left end wall, right end wall, X-ray window 8, alignment guide 2, electrical connector 3, an alignment hole, threaded stud, threaded hole, threaded nut, nut mounting post, nut connector. X-ray tube assembly 1 enclosure has an enclosure body. Module cover includes a cutout on the top surface so that the X-ray window 8 can be visible outside the X-ray tube assembly 1 enclosure.

The enclosure is made of low-cost extrusion aluminum. End flanges are welded to main enclosure body to avoid fluid leak. The connector is made in such a way that it is has good electrical contact and good fluid seal on the end flanges. Connector usually has electrical power connectors and X-ray control connectors for driving high voltage power supply, usually one set of the electrical power connector, but it can have multiple sets. The pins are built into matching connectors inside the enclosure. The enclosure is mostly filled with standard X-ray tube insulation oil for both insulation and cooling. The enclosure also has an internal electronic shielding structure and a high voltage driver circuit. However, it can still improve the reliability of this system because there is built-in diagnostics to find out what happened to the X-ray tube 5. Also, it is good for long-term use of the system because lifetime statistics are tracked electronically. Therefore, for the replacement process, no special training is needed for the most part of it. If needed, most of the replacement processes are only plug-and-play activities that anyone can do without special training.

There are three main differences from prior art monoblock type and portable type modular X-ray sources. First, consumable parts such as an X-ray tube 5, a high voltage circuit board 6 and insulation oil are all arranged inside a pre-designed enclosure. All other parts are outside of the enclosure. Second, there is an alignment guide 2 at the back of the enclosure to help to position a replacement X-ray tube assembly 1. Alignment guide 2 and electrical connector 3 on the enclosure provide for easy and rapid replacement of X-ray tube assembly 1. Third, other electrical parts are modularized in the form of a removable PCB board.

The modular X-ray source that can be inserted into a motion compensated multiple pulsed X-ray source tomosynthesis imaging system 11 to replace the traditional monoblock type of X-ray sources. The modular X-ray source contains an X-ray tube 5, high voltage circuit board 6, insulation, and cooling oil inside the module enclosure structure. An X-ray tube 5 has the following features: The housing of the X-ray tube 5 should be sealed against the environment because the X-ray tube 5 is capable of creating X-rays. On one end of the X-ray tube 5 is the window for X-ray emission. On the other end of the X-ray tube 5 is a connector for electrical connection. One or more support structures should be installed inside the X-ray tube housing. It should have electrical conductors running from the X-ray tube pins through the housing to the outside of the X-ray tube. In addition, there should be a ballast mounted on the inside of the X-ray tube housing. A control panel or any other equipment could be mounted on the outside of the X-ray tube assembly 1 enclosure. There should be a guidepost mounted on the X-ray tube assembly 1 enclosure so that it can be easily located for alignment.

A pre-designed, simple to assemble, cost-effective, standardized, multi-source modular X-ray source assembly. The system has a better service life, higher reliability, and lower cost. There are high-voltage electrical connectors inside the enclosure for connecting to a high voltage circuit board 6 inside the enclosure. (a). When assembling, the user first assembles on both ends of the enclosure and weld into one body. High voltage cables or bus bars go through two holes on the enclosure on each end and connect to the X-ray tube 5 and high voltage circuit board 6. High voltage connectors on each end of the enclosure can be detached for this purpose. (b). On the side of the enclosure, there is an alignment guide 2 that connects to high voltage circuit as well as electrical connectors 3. It is also used for alignment and high voltage DC adjustment. (c). Then X-ray tube 5 and related components will be installed inside the enclosure. An alignment tool is usually provided with each source so the user can adjust and align easily and efficiently before installing the final assembly.

Figure 2:
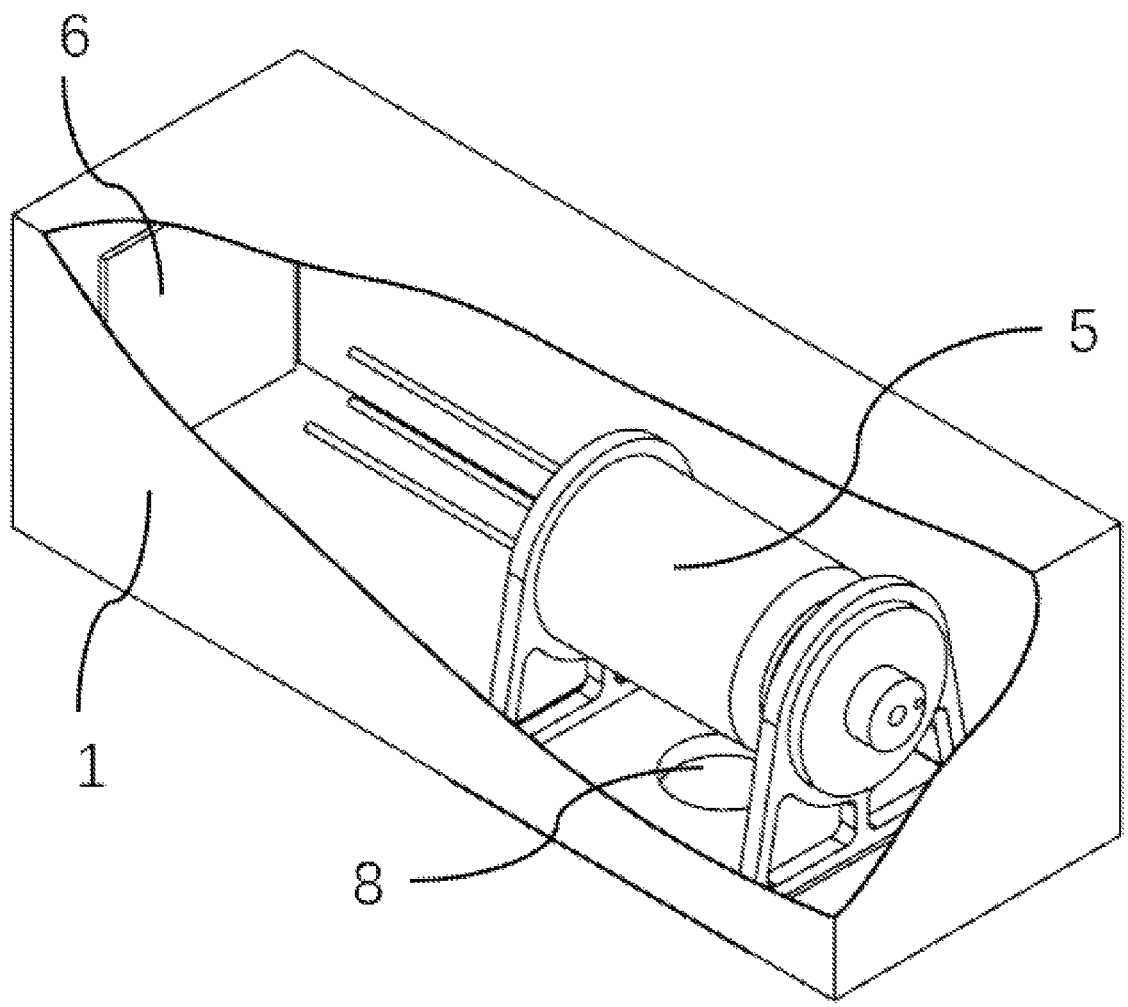
FIG. 2 illustrates details inside a replaceable X-ray tube assembly of modular X-ray source.

In one embodiment, FIG. 2 shows that X-ray tube assembly 1 is designed in such a way it can be easily replaced. The X-ray tube 5 is located inside a robust enclosure with holder support. The enclosure has an X-ray window 8. The electrical board includes a high voltage generation part of the X-ray tube 5 is also located inside the enclosure. The X-ray tube 5 is surrounded by high voltage oil. The oil also provides the cooling capability. The enclosure usually is made of low-cost extrusion aluminum and is welded together to seal at both ends.

A holder support is mounted to the support arm in such a way that the holder support is movable with respect to the support arm along the longitudinal axis of the support arm. Holder has an X-ray tube 5 attached thereto. The X-ray tube 5 is installed in the holder by means of appropriate flanges, screws or other appropriate fixing means so that the X-ray tube 5 can be moved along the longitudinal axis of the holder. X-ray tube 5 is connected to the electrical power supply via cables. A high voltage circuit is connected to the electrical power supply via cables. Thus, the modular X-ray source comprises the following main components: 1) low voltage power and control; 2) high voltage circuit board 6; 3) X-ray tube assembly 1; 4) enclosure for X-ray tube assembly 1. The modular X-ray source can be made to fit different multiple source imaging systems because the parts are prefabricated offsite. It can save time and money when all parts arrive at the site together.

The enclosure contains high voltage circuit board 6 and X-ray tube 5 for operation. The X-ray tube 5 that has electrodes and on its two ends, also called cathode and anode. The electrode is the larger one than the electrode. The electrodes and are arranged to face each other within a space inside the enclosure at a certain distance. A high voltage circuit board 6 provides high voltage to the electrodes and create X-ray emission. A high voltage can be tens of kilovolts. Electrical connectors are located at the end of the enclosure. Alignment guide is needed for connector contact. An insulating coating later covers the connector guide after it performs its role.

The present system is modular and user-replaceable since the entire X-ray tube assembly inside enclosure can be swapped out just like a lightbulb. The X-ray tube and high voltage circuit and cooling insulating oil and X-ray tube alignment are all arranged inside a pre-designed module enclosure structure. There is an X-ray window 8, alignment guide, and electrical connectors 3 on the module enclosure structure. The enclosure usually is made of low-cost extrusion aluminum and welded at both ends. On the module enclosure structure, there is X-ray window 8, alignment guide 2 and electrical connectors 3. The enclosure usually is made of low-cost extrusion aluminum and welded at both ends. X-ray tube 5 and cooling, insulating oil are placed inside the enclosure structure. X-ray tube 5 and cooling, insulating oil are placed inside enclosure structure and the entire assembly is replaced for maintenance purposes. The modular X-ray module is particularly useful for motion compensated multiple source tomosynthesis imaging systems 11 where multiple pulsed X-ray sources are utilized because it enables easy replacement of X-ray tube assembly 1, lower maintenance cost, reliable X-ray imaging system where fast and durable operating time is required.

The modular user-replaceable X-ray modules enable easy replacement/maintenance. One exemplary maintenance process includes the following: Step A. Disconnecting power supply; Step B. Unlocking the security latch of the locking of the enclosure; Step C. Pulling X-ray tube assembly 1 along connector guide of the enclosure; Step D. Inserting of a new X-ray tube assembly 1 along connector guide of the enclosure; Step E. Lockdown both ends of the locking bars to keep the security locking in place. Then the X-ray tube assembly 1 is ready for operation. The installation is quite simple.

It takes about one minute to replace the entire X-ray assembly 1, thus maintenance costs can be lowered dramatically. Also, when a real replacement job happens, this process does not need special skills from a technician. Pushing the new X-ray assembly 1 enclosure along with connector guide and locking the security latch. Security latches can lock two enclosure sides together. An alignment guide 2 with a window will help to guide the correct position of the new enclosure. This guide will be hidden once the connector guide is pushed through the enclosure sides.

Figure 5:
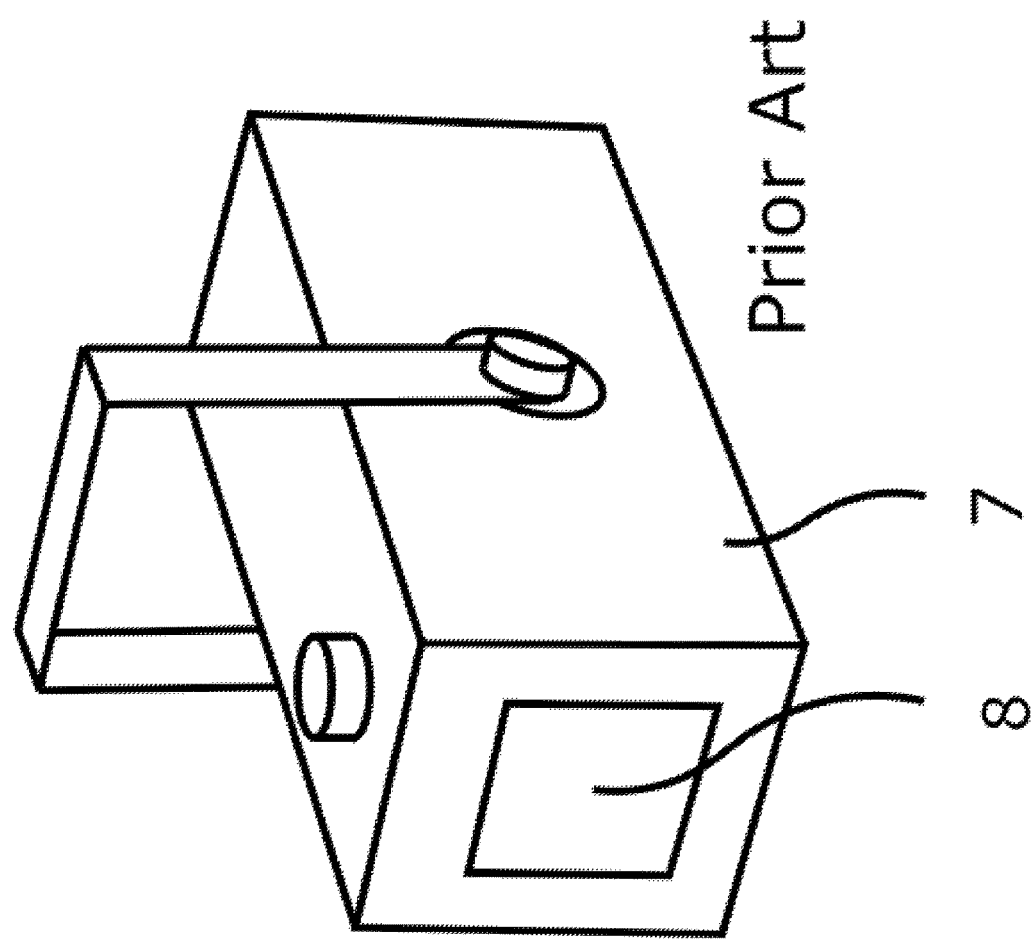
FIG. 5 shows a conventional low power portable X-ray source as one of prior arts.

FIG. 5 shows another type of conventional compact portable whole X-ray source 7 in prior art. X-ray window 8 is at the front. Low voltage electrical control, high voltage generators and X-ray tube 5 are all built inside an even smaller size enclosure. The microcontroller is also built in the enclosure. The microcontroller controls the voltage, exposure time, and other settings. Usually, it can also be battery powered.

Figure 6:
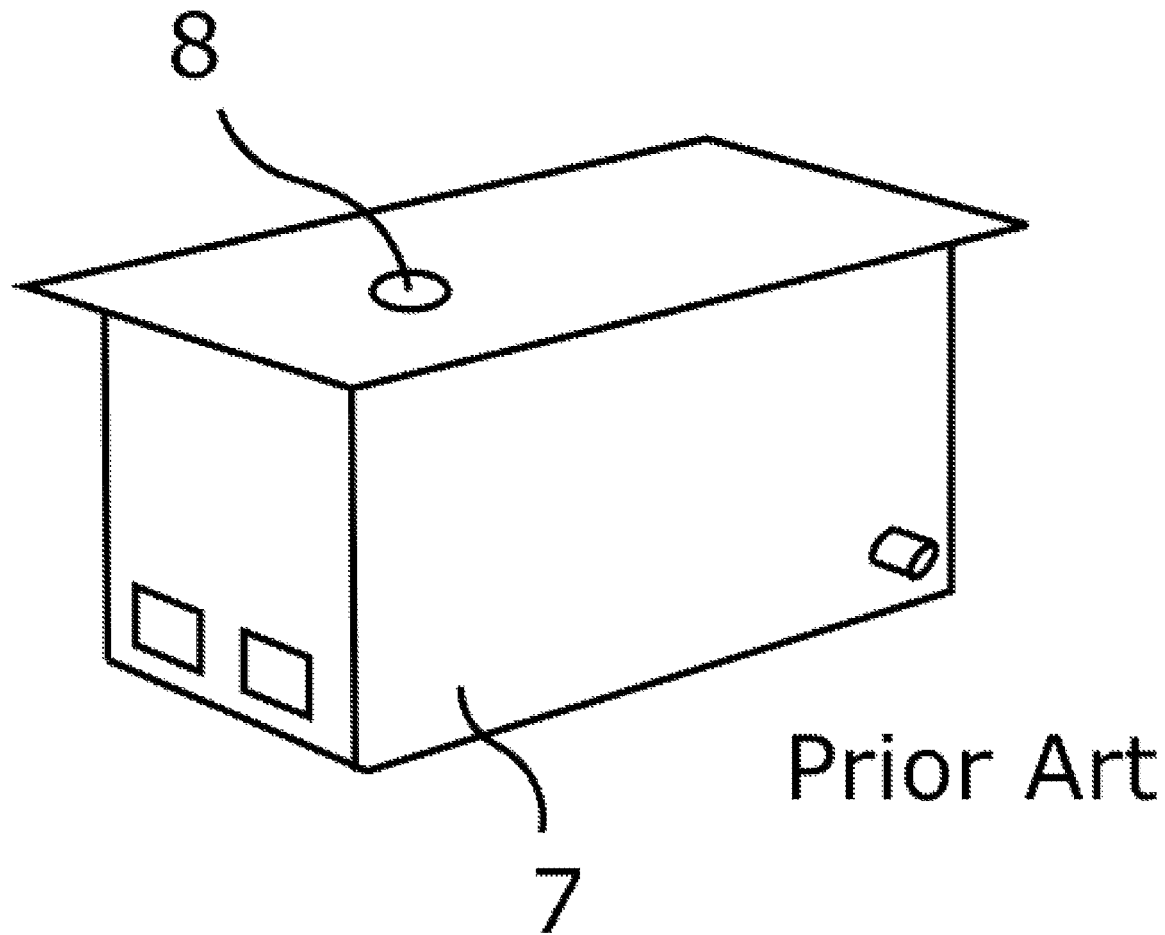
FIG. 6 shows a conventional mono-block X-ray source as one of prior arts.

FIG. 6 shows the type of a one-body whole X-ray source 7 in prior art, it is usually called mono-block. X-ray window 8 is at the middle of body. In a mono-block body, a high voltage generator, low voltage electrical control and X-ray tube are all also built inside a smaller solid enclosure. There are power connectors. There are also connectors to link to an outside device or a PC to send or receive commands. A mono-block type whole X-ray source 7 can have higher power than compact portable whole X-ray source 7.

Various modifications and alterations of the invention will become apparent to those skilled in the art without departing from the spirit and scope of the invention, which is defined by the accompanying claims. It should be noted that steps recited in any method claims below do not necessarily need to be performed in the order that they are recited. Those of ordinary skill in the art will recognize variations in performing the steps from the order in which they are recited. In addition, the lack of mention or discussion of a feature, step, or component provides the basis for claims where the absent feature or component is excluded by way of a proviso or similar claim language.

While various embodiments of the present invention have been described above, it should be understood that they have been presented by way of example only, and not of limitation. The various diagrams may depict an example architectural or other configuration for the invention, which is done to aid in understanding the features and functionality that may be included in the invention. The invention is not restricted to the illustrated example architectures or configurations, but the desired features may be implemented using a variety of alternative architectures and configurations. Indeed, it will be apparent to one of skill in the art how alternative functional, logical or physical partitioning and configurations may be implemented to implement the desired features of the present invention. Also, a multitude of different constituent module names other than those depicted herein may be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Terms and phrases used in this document, and variations thereof, unless otherwise expressly stated, should be construed as open ended as opposed to limiting. As examples of the foregoing: the term "including" should be read as meaning "including, without limitation" or the such as; the term "example" is used to provide exemplary instances of the item in discussion, not an exhaustive or limiting list thereof; the terms "a" or "an" should be read as meaning "at least one," "one or more" or the such as; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Hence, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other such as phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, may be combined in a single package or separately maintained and may further be distributed across multiple locations.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

The invention claimed is:

1. A modular X-ray source assembly apparatus for a motion compensated multiple pulsed X-ray source tomosynthesis imaging system, comprising:
    a plurality of multi-pin connectors on respective enclosures to drive a high voltage circuit, to control a filament, to get high voltage feedback and to measure temperature;
    a plurality of connector engagement alignment guides; and
    a plurality of modular and user replaceable modules each coupled to the respective multi-pin connector and including:
        a plurality of high-voltage generating circuit boards inside the respective enclosure; and
        a connector adapted to be coupled to the respective multi-pin connector,
    wherein the user replaceable modules comprise X-ray sources adapted to be mounted on a primary motor stage moving on an arc rail with a motor that engages and controls a speed of the primary motor stage, and when an individual X-ray source has a speed equal to a group source speed, but with an opposite moving direction, the individual X-ray source and an X-ray detector are activated with an exposure control unit.

2. The apparatus of claim 1, wherein the enclosures are replaceable in the multi-source tomosynthesis imaging system with multiple pulsed X-ray sources.

3. The apparatus of claim 1, wherein the enclosures are metal and welded together to seal at both ends.

4. The apparatus of claim 1, wherein the X-ray sources are surrounded by high voltage insulating oil and wherein the oil cools the X-ray sources.

5. The apparatus of claim 1, wherein an X-ray window is welded on one end of the respective enclosure and an alignment guide is on another end of the respective enclosure.

6. The apparatus of claim 1, comprising electrical connectors on one end of the respective enclosure.

7. The apparatus of claim 1, comprising a cooling insulating oil injected into the respective enclosure through a filling hole at the end of the enclosure to fill a space between the respective X-ray source and an X-ray source window, where the X-ray source is installed thereafter.

8. The apparatus of claim 1, comprising a holder support mounted to a support arm, where the holder support is movable relative to the support arm along a longitudinal axis of the support arm.

9. The apparatus of claim 8, wherein the respective X-ray source is installed in the holder and wherein the respective X-ray source is moveable along a longitudinal axis of the holder.

10. The apparatus of claim 1, comprising an aluminum enclosure filled with oil for high voltage insulation and cooling.

11. A method to perform multiple pulsed X-ray source tomosynthesis imaging with a system, wherein a modular X-ray source of the system is inside an enclosure that is user replaceable, the modular X-ray source including an X-ray window positioned on the enclosure; an X-ray source inside the enclosure and facing the X-ray window; one or more high-voltage generating circuit boards inside the enclosure; and a connector adapted to be coupled to a multi-pin connector, and wherein the system comprises user replaceable X-ray sources adapted to be mounted on a primary motor stage moving on an arc rail with a motor that engages and controls a speed of the primary motor stage, and when an individual X-ray source has a speed equal to a group source speed, but with an opposite moving direction, the individual X-ray source and an X-ray detector are activated with an exposure control unit, the method further comprising:
    turning off an X-ray source power;
    unlocking one or a plurality of security latches;
    pulling the enclosure including the modular X-ray source assembly to detach; and
    pushing a new enclosure with a new X-ray source assembly along a connector guide and locking the respective security latch.

12. The method of claim 11, wherein the respective X-source is user-replaceable in the multi-source tomosynthesis imaging system with multiple pulsed X-ray sources.

13. The method of claim 11, wherein the enclosure is metal, further comprising welding and sealing the enclosure at both ends.

14. The method of claim 11, wherein the X-ray sources are surrounded by high voltage insulation oil and wherein the oil cools the X-ray sources.

15. The method of claim 11, wherein the X-ray window is welded on one end of the enclosure and an alignment guide is on another end of the enclosure.

16. The method of claim 11, comprising connecting electrical connectors on one end of the enclosure.

17. The method of claim 11, comprising injecting cooling insulating oil into the enclosure through a filling hole at one end of the enclosure and draining the oil into a space between the X-ray source and the X-ray source window and installing an X-ray source thereafter.

18. The method of claim 11, comprising mounting a holder support to a support arm, where the holder support is movable relative to the support arm along a longitudinal axis of the support arm.

19. The method of claim 18, wherein the X-ray source is installed in the holder and wherein the X-ray source is moveable along a longitudinal axis of the holder.

* * * * *